United States Patent
Evans et al.

(10) Patent No.: US 12,232,870 B2
(45) Date of Patent: *Feb. 25, 2025

(54) SYSTEMS AND METHODS OF OPTICAL TRANSCUTANEOUS OXYGENATION MONITORING

(71) Applicant: The General Hospital Corporation, Boston, MA (US)

(72) Inventors: Conor Evans, Charleston, MA (US); Nicholas Nowell, Somerville, MA (US); Emmanouil Rousakis, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,687

(22) Filed: Aug. 5, 2022

(65) Prior Publication Data

US 2023/0113642 A1    Apr. 13, 2023

Related U.S. Application Data

(63) Continuation of application No. 16/300,009, filed as application No. PCT/US2017/032650 on May 15, 2017, now Pat. No. 11,406,297.

(Continued)

(51) Int. Cl.
*A61B 5/1455*    (2006.01)
*A61B 5/00*    (2006.01)
(Continued)

(52) U.S. Cl.
CPC ........ *A61B 5/14552* (2013.01); *A61B 5/0082* (2013.01); *A61B 5/145* (2013.01);
(Continued)

(58) Field of Classification Search
CPC ... A61B 5/14552; A61B 5/0082; A61B 5/145; A61B 5/1455; A61B 2562/046;
(Continued)

(56) References Cited

U.S. PATENT DOCUMENTS

| | | |
|---|---|---|
| 4,041,932 A | 8/1977 | Fostick |
| 5,030,420 A | 7/1991 | Bacon et al. |

(Continued)

FOREIGN PATENT DOCUMENTS

| | | |
|---|---|---|
| WO | 9603074 A1 | 2/1996 |
| WO | 2014011724 A1 | 1/2014 |

(Continued)

OTHER PUBLICATIONS

European Patent Office, Extended European Search Report, Application No. 17797019.1, Dec. 2, 2019, 8 pages.

(Continued)

*Primary Examiner* — Michael R Bloch
*Assistant Examiner* — Abid A Mustansir
(74) *Attorney, Agent, or Firm* — Quarles & Brady LLP (57) ABSTRACT

Systems and methods of optical transcutaneous oxygenation monitoring. The oxygenation monitor comprises a photoluminescent oxygen-sensitive probe, a photon source positioned to direct photons at the probe, a photodetector positioned to detect light emitted from the probe when the photon source directs photons at the probe, a controller in electrical communication with the photon source and the photodetector, the controller being configured to execute a program stored in the controller to calculate a level of oxygen adjacent the probe from an electrical signal received from the photodetector. The photon source, the photodetector, and the controller are disposed in or on a support structure.

30 Claims, 3 Drawing Sheets

Related U.S. Application Data (60) Provisional application No. 62/335,961, filed on May 13, 2016.

(51) Int. Cl.
*A61B 5/145* (2006.01)
*A61M 5/172* (2006.01)

(52) U.S. Cl.
CPC ........... *A61B 5/1455* (2013.01); *A61M 5/172* (2013.01); *A61M 5/1723* (2013.01); *A61B 2562/046* (2013.01); *A61M 2205/502* (2013.01); *A61M 2230/205* (2013.01)

(58) Field of Classification Search
CPC ................ A61M 5/172; A61M 5/1723; A61M 2205/502; A61M 2230/205
See application file for complete search history.

(56) References Cited

U.S. PATENT DOCUMENTS

| | | |
|---|---|---|
| 5,127,405 A | 7/1992 | Alcala et al. |
| 5,151,869 A | 9/1992 | Alcala et al. |
| 5,315,993 A | 5/1994 | Alcala et al. |
| 5,628,310 A | 5/1997 | Rao et al. |
| 2006/0241364 A1 | 10/2006 | Ince |
| 2007/0172392 A1* | 7/2007 | Sen ..................... A61B 5/14556 422/82.08 |
| 2010/0234706 A1* | 9/2010 | Gilland .............. A61B 5/14552 600/344 |
| 2011/0105869 A1 | 5/2011 | Wilson et al. |
| 2011/0201802 A1* | 8/2011 | Tobita .................... G01N 33/84 540/3 |
| 2015/0182166 A1 | 7/2015 | Evans et al. |
| 2015/0190080 A1 | 7/2015 | Ashkenazi |
| 2015/0217056 A1* | 8/2015 | Kadavy ................ A61H 31/006 128/202.16 |
| 2016/0159842 A1 | 6/2016 | Evans et al. |
| 2016/0338631 A1 | 11/2016 | Li et al. |

FOREIGN PATENT DOCUMENTS

| | | |
|---|---|---|
| WO | 2015006015 A1 | 1/2015 |
| WO | 2015163957 A2 | 10/2015 |

OTHER PUBLICATIONS

PCT International Search Report and Written Opinion, PCT/US2017/032650, Aug. 1, 2017, 13 pages.

* cited by examiner

SYSTEMS AND METHODS OF OPTICAL TRANSCUTANEOUS OXYGENATION MONITORING

CROSS-REFERENCES TO RELATED APPLICATIONS

This application is a continuation of U.S. patent application Ser. No. 16/300,009 filed Nov. 8, 2018, which is a U.S. National Phase of Application PCT/US2017/032650 filed on May 15, 2017, which claims priority from U.S. Patent Application No. 62/335,961 filed May 13, 2016.

STATEMENT REGARDING FEDERALLY SPONSORED RESEARCH

Not Applicable.

BACKGROUND OF THE INVENTION

1. Field of the Invention

The current invention relates to systems and methods of oxygenation monitoring, specifically optical transcutaneous oxygenation monitoring.

2. Description of the Related Art

Oxygen is crucial for wound healing and is required during wound repair for a host of processes including epithelial cell migration, collagen synthesis, fibroblast proliferation, and neutrophil influx to stave off infection. Molecular oxygen is the final, most essential component of aerobic respiration, the primary means of energy generation in all human tissue. Given its importance to the survival of tissue, a rapid, noninvasive means of determining tissue oxygenation would be enormously useful in clinical assessment and decision-making.

A number of technologies have been developed to assess perfusion, and indirectly, tissue oxygenation. Indocyanine green angiography and xenon-133 angiography, for example, take only a few minutes and provide a very clear assessment of perfusion in a given region. However, angiography requires blood flow and injection of an exogenous agent, not to mention a bulky detection apparatus. Clark electrodes, the gold standard for oxygen sensing, provide only a point measurement and are rather invasive. Near-infrared spectroscopy (NIRS) has had fantastic success in predicting graft and flap failure during and after reconstructive surgery, but is prohibitively expensive and too sensitive to changes in overhead lighting, placement on the skin, and anesthesia. Devices that measure local blood oxygen saturation ($StO_2$) have provided insight into wound and graft health, but only measure the binding of oxygen to heme, not tissue oxygenation. In chronic wounds of the lower limbs, common co-morbidities like medial calcinosis, peripheral vascular disease, diabetes, and chronic renal failure confound beyond any usability traditional metrics of perfusion, such as blood pressures, color, temperature, and capillary refill. All in all, while many technologies exist for monitoring perfusion or oxygenation, none seems to be completely effective and compatible with current clinical workflows. Despite the numerous forays into oxygen sensing, there is still an unmet need among clinicians for an easy-to-use tool for efficiently determining tissue oxygenation.

Transcutaneous oximetry (TCOM), an electrode-based technique for quantifying local $pO_2$, has the greatest potential to be a broad, multi-use tool in a wide array of clinical settings, particularly those focused on wound care. TCOM has been proven over several decades to be an effective tool for the prediction of wound healing and, more generally, tissue oxygenation as a whole. In chronic wounds, where it is perhaps most often used, TCOM has shown excellent predictive power, both in determining whether a wound will close on its own or necessitate amputation, as well as whether or not a wound will respond to hyperbaric oxygen therapy (HBO). TCOM can be used to create a risk score for chronic wounds to predict whether they will heal without major intervention and to guide treatment decisions. Similarly, since neonates are notoriously sensitive to changes in oxygenation, TCOM has been applied to neonatal monitoring with some success. Often, major surgical decisions rest on the outcome of a TCOM measurement: in chronic wound clinics, podiatrists attempt to interpret TCOM data to determine the extent of tissue amputations. In the case of HBO, if the transcutaneous $pO_2$ near the wound is above a certain threshold, typically 10 mmHg, or increases noticeably upon supplemental oxygen administration and re-measurement, the wound will typically respond to HBO. If a negative response is found, the clinicians then need to explore more significant interventions, such as further debridement, antibiotics, or even amputation.

Yet despite their potential and promise in literature, today's electrode-based TCOM devices see scant and diminished use in actual current clinical practice. Discussions with clinicians, as well as reviews in literature, suggest the primary drawbacks of TCOM are its need for extensive, time-consuming bedside calibration, heating of tissue to 43-45 degrees Celsius (at some discomfort to the patient), a trained operator, and a rather long duration for use, requiring anywhere from 15 to 45 minutes for a single measurement. Expensive to own and operate, the use of TCOM devices has dwindled over the past decade as technicians, clinicians, and hospitals avoid the complex technology. All these limitations arise from the core, decades-old oxygen electrode technology on which TCOM devices operate.

Despite the paramount importance of oxygen in tissue metabolism, devices currently used in patient monitoring measure $SpO_2$ or $StO_2$, the oxygen saturation of hemoglobin in arterial blood, or in capillaries underlying tissue, respectively. While adequate for measuring systemic oxygenation, these metrics provide only indirect information regarding the oxygenation of specific regions of tissue. Transcutaneous oxygen measurement (TCOM, or $TcpO_2$) is a noninvasive technique used in wound care and surgical setting to record the oxygen concentration, or partial pressure of oxygen ($pO_2$), at the skin surface. Current TCOM devices, however, require approximately 20 minutes of bedside calibration, heating of tissue to approximately 45° C. (known to cause burns and discomfort), and a well-trained operator. These limitations have hamstrung TCOM, rendering it an unwieldy technique, instead of the broad, versatile, multi-platform tissue oxygen sensor it could be. Primary market research with wound care and podiatric physicians shows that clinicians need the information provided by TCOM—the oxygenation of tissue, an excellent measurement of overall tissue viability—but do not or cannot use existing burdensome TCOM devices in the clinic.

Therefore, there exists a need for systems and methods of oxygenation monitoring, specifically optical transcutaneous oxygenation monitoring.

SUMMARY OF THE INVENTION

The present invention relates to systems and methods of oxygenation monitoring, specifically optical transcutaneous oxygenation monitoring.

Optical methods for tissue analysis offer considerable benefits for research and clinical practice, including the ability to carry out noninvasive and painless tissue property assessment, the ability to rapidly acquire data from tissue with minimal to no preparation time, and the ability to create miniaturized and even wearable toolkits.

In some embodiments, an oxygenation monitor is provided for use with a photoluminescent oxygen-sensitive probe. The oxygenation monitor comprises a photon source configured to direct photons at the probe; a photodetector configured to detect light emitted from the probe when the photon source directs photons at the probe; a controller in electrical communication with the photon source and the photodetector, wherein the controller is configured to execute a program stored in the controller to calculate a level of oxygen adjacent the probe from an electrical signal received from the photodetector; and a support structure. The photon source, the photodetector, and the controller are disposed in or on the support structure. The support structure can be a substrate, and the photon source, the photodetector, and the controller can be embedded in the substrate.

The oxygenation monitor can comprise a photoluminescent oxygen-sensitive probe. In some embodiments, the photoluminescent oxygen-sensitive probe can be a formulation having an emission that provides tissue $pO_2$. The photoluminescent oxygen-sensitive probe can comprise a polymeric material impregnated with a porphyrin. The photoluminescent oxygen-sensitive probe can comprise a polymer impregnated with a phosphorescent meso-unsubstituted porphyrin. The photoluminescent oxygen-sensitive probe can comprise a green-emitting dye that can serve as a reference standard for precise $pO_2$ measurements. The photoluminescent oxygen-sensitive probe can emit red phosphorescence when excited by blue light from the photon source. A phosphorescence intensity detected by the photodetector can be inversely proportional to $pO_2$ of the tissue of a patient.

In some embodiments, the photoluminescent oxygen-sensing probe can comprise both a red-emitting, oxygen sensitive probe and a green-emitting reference dye, both the red-emitting, oxygen sensitive probe and the green-emitting reference dye can be simultaneously excited by blue light from the photon source.

In some embodiments, the photon source can be a blue light-emitting diode. In other embodiments, the photon source can be an orange light-emitting diode.

In some embodiments, the detectors can be a photodiode, photomultiplier tube, avalanche photodiode, charge-coupled device (CCD), complementary metal-oxide semiconductor (CMOS) device, or combination of similar photodetectors.

In some embodiments, the photodetector can be one or more red sensitive photodiode detectors. The photodetector can comprise one or more red sensitive photomultiplier tubes. The photodetector can comprise one or more red sensitive avalanche photodiode detectors. The photodetector can comprise one or more red sensitive charge-coupled devices (CCD). The photodetector can comprise one or more red sensitive complementary metal-oxide semiconductor (CMOS) devices.

In some embodiments, the photodetector can be one or more green sensitive photodiode detectors. The photodetector can comprise one or more green sensitive photomultiplier tubes. The photodetector can comprise one or more green sensitive avalanche photodiode detectors. The photodetector can comprise one or more green sensitive charge-coupled devices (CCD). The photodetector can comprise one or more green sensitive complementary metal-oxide semiconductor (CMOS) devices.

In some embodiments, the support structure can be a flexible circuit board attached to a surface of the photoluminescent oxygen-sensitive probe via an oxygen-impermeable membrane. In other embodiments, the support structure can be a flexible circuit board attached to the surface of the photoluminescent oxygen-sensitive probe. The support structure can be made by an oxygen-impermeable material to serve as an impermeable membrane.

In some embodiments, an oxygen-dependent change in red phosphorescence intensity can be captured by one or more red sensitive photodiode detectors. The oxygen-dependent change in red phosphorescence intensity can be referenced against a green emission intensity captured by one or more green sensitive photodiode detectors using an analog or digital processing of the controller to provide transcutaneous oxygen measurements of the tissue of the patient.

In some embodiments, an oxygen-dependent change in phosphorescence lifetime can be captured by one or more photosensors, with the lifetime processed using analog or digital circuitry or analog or digital analysis of the controller to provide transcutaneous oxygen measurement of the tissue of the patient.

In some embodiments, the controller can comprise an analog circuitry that can provide pre-calibrated, transcutaneous oxygen tension measurements of the tissue of the patient using a Stern-Volmer relationship. The level of oxygen adjacent the probe can be reported by utilizing one or more fluorophore probes and one or more phosphor probes, the emission properties of the fluorophore probes can be insensitive to oxygen, and the emission properties of phosphor probes are influenced by molecular oxygen concentration. The oxygenation monitor can be an optical transcutaneous oxygenation monitor. The oxygenation monitor can be implantable in a body part of a patient. The implantable monitor can comprise an implantable substrate containing the porphyrin sensor with the emission of the implantable sensor detected by photosensors placed separately from the implantable sensor.

In some embodiments, the photoluminescent oxygen-sensitive probe is removably attached to the support structure. The oxygenation monitor can further comprise a display in electrical communication with the controller, wherein the controller is configured to execute the program stored in the controller to display the level of oxygen on the display. The controller can be configured to execute the program stored in the controller to store values of the level of oxygen at a plurality of times over a time period. The controller can be configured to execute the program stored in the controller to display values of the level of oxygen at a plurality of times over a time period.

In some embodiments, the support structure can be a container housing the photon source, the photodetector, and the controller, and the excitation and emission light can be transmitted between the probe and the photon source and the photodetector via light guides, such as optical fibers. The photon source can direct photons at the probe via an optical fiber, and the photodetector can detect light emitted from the probe via an optical fiber.

In some embodiments, a kit for monitoring oxygenation is provided. The kit comprises an oxygenation monitor of any of the embodiments of this disclosure, and one or more photoluminescent oxygen-sensitive probes, wherein the photoluminescent oxygen-sensitive probes are structured to be removably attached to the support structure. The oxygenation monitor may include a band structured for securing the support structure to a body part of a patient. Each photoluminescent oxygen-sensitive probe can comprise a polymeric material impregnated with a porphyrin. Each photoluminescent oxygen-sensitive probe can comprise a polymer, wherein non-limiting examples include silicone, nitrocellulose, or polymethylmethacrylate, impregnated with a phosphorescent meso-unsubstituted porphyrin. Each photoluminescent oxygen-sensitive probe can be provided in a package that does not transmit photons of a wavelength that causes emission of light by the probe. The package can include an indicator of the useful lifetime of the photoluminescent oxygen-sensitive probe.

In some embodiments, a device is provided that comprises a medical instrument, and an oxygenation monitor of any of the embodiments of this disclosure. The oxygenation monitor can be attached to the medical instrument. The medical instrument can be a catheter. The device can comprise a display in electrical communication with the controller of the oxygenation monitor, wherein the controller is configured to execute the program stored in the controller to display the level of oxygen on the display.

In some embodiments, an optically-based oxygen sensor to replace TCOM in the marketplace is provided. This dramatically less expensive product, which requires no heating, bedside calibration, or training, is immediately adaptable into existing clinical workflows and early prototypes have already been validated in animal models of inflammation, ischemia-reperfusion injury, burns, and grafts. This product can be utilized for peri-operative assessment and post-operative monitoring during operations that aim to improve or restore tissue perfusion, including wound debridement, grafts, and amputations.

In some embodiments, to overcome these obstacles and deliver on the full promise of TCOM, an optical transcutaneous oxygen monitoring approach that builds upon oxygen-sensing bandage technologies is provided. This TCOM system can comprise a pad-like sensor with an LED and a detector that can be mounted on a small patch of light-based oxygen sensing formulation, whose emission provides tissue $pO_2$. Since this approach directly measures $pO_2$, not blood flow or hemoglobin binding to oxygen, it does not require perfusion or underlying blood vessels, and is therefore less prone to failure than NIRS or Doppler-based sensing systems. All sensing components can be safely retained within the non-invasive optical TCOM system, and as such, exogenous dyes, injectable agents, and needles are not required. Requiring essentially no preparation time, readout of the optical TCOM device can be essentially instantaneous. With no bedside calibration, no heating, no need for underlying blood flow, a simple readout, no unwieldy equipment, and minimal equilibration time before getting results, the optical TCOM system can be uniquely positioned to address the problems that plague TCOM and clinical oxygen sensing as a whole.

These and other features, aspects, and advantages of the present invention will become better understood upon consideration of the following detailed description, drawings, and appended claims.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined by the claims. The features illustrated or described in connection with one exemplary embodiment may be combined with the features of other embodiments. Such modifications and variations are intended to be included within the scope of the present invention.

Figure 1:
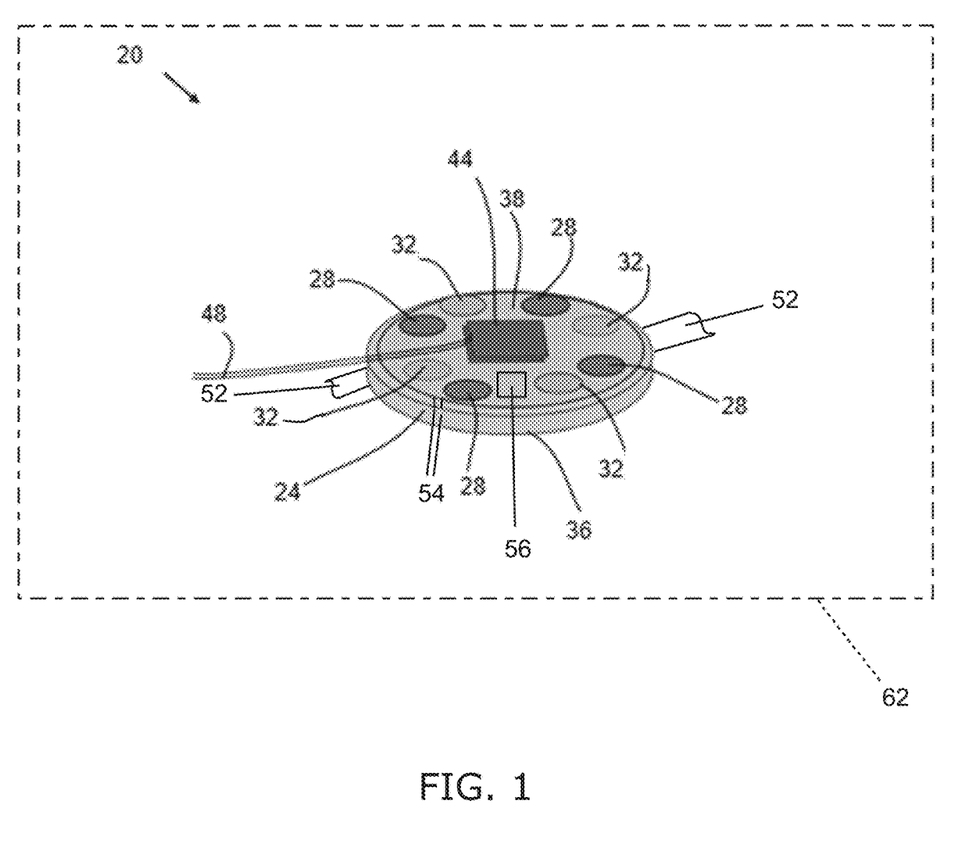
FIG. 1 is a perspective view of an oxygenation sensor according to an embodiment of this disclosure.

FIG. 1 shows one embodiment of an optical transcutaneous oxygen monitoring system 20 (optical TCOM system 20) of this disclosure. The optical TCOM system 20 can incorporate a probe 24 that can have a light-based oxygen sensing formulation that can have an emission that can provide tissue $pO_2$, emission sources 28, and detectors 32 that can be mounted on the optical TCOM system 20. Since optical TCOM system 20 can directly measure $pO_2$, it does not require perfusion or underlying blood vessels. The sensing components can be safely retained within the optical TCOM system 20, which can be non-invasive, and as such, exogenous dyes, injectable agents, and needles may not be required. The optical TCOM system 20 can require low preparation time, and a readout of the optical TCOM system 20 can be essentially instantaneous. With the optical TCOM system 20, bedside calibration and heating may not be required, underlying blood flow may not be needed, and minimal equilibration time before getting results that can be presented on a simple readout, thereby providing a solution to the problems that plague TCOM and clinical oxygen sensing as a whole.

The optical TCOM system 20 can have an interface mechanism 36 that can be configured to place the optical TCOM system 20 in contact with a tissue of a patient. In some embodiments, the interface mechanism 36 can provide contact between the optical TCOM system 20 and a tissue of the patient using an adhesive that adheres an interface surface 36 of the optical TCOM system 20 to the tissue of the patient. The interface mechanism 36 in the form of an adhesive can directly and reversibly adhere the optical TCOM system 20 to the tissue of the patient. In other embodiments, the interface mechanism 36 can be a strap, a band 52, an elastic element, a pocket, or any other suitable interface mechanism 36 capable of placing the optical TCOM system 20 in contact with a tissue of a patient.

The optical TCOM system 20 can also have a probe 24 that can have a light-based, photoluminescent oxygen sensing formulation that can have an emission that can provide tissue $pO_2$. The probe 24 can be an oxygen-sensing polymer or polymer containing an oxygen-sensing molecule that can be positioned to be in contact with or coincident with the interface surface 36 of the optical TCOM system 20 such that the probe 24 can be in direct contact with the tissue of the patient. The probe 24 can be in the form of a cylindrical silicon pad infused with oxygen sensing molecules. The cylindrical silicon pad can also contain other sensors such as reference sensors. The reference sensors can provide a baseline for oxygenation measurement or a reference for calibrating the oxygen sensor.

Silicones, in particular polydimethylsiloxane (PDMS), can be extremely gas-permeable and can allow rapid readout of tissue oxygen dynamics. The silicone polymer of the probe 24 can be impregnated with brightly emissive, porphyrin-based, oxygen-sensing molecules. The oxygen-sensing molecules embedded in the probe 24 can be photoluminescent oxygen-sensing molecules. For example, the oxygen-sensing molecules can emit red phosphorescence when excited by blue light, and the phosphorescence intensity can be inversely proportional to $pO_2$. A reference sensor in the form of a green-emitting dye can also be incorporated into the silicone of the probe 24 to serve as a reference standard for precise $pO_2$ measurements.

In some embodiments, the probe 24 can comprise porphyrin-based, oxygen sensing molecules designed to provide extremely high sensitivity and accuracy for the measurement of tissue oxygenation. The porphyrin-based, oxygen sensing molecules can be built via a modular synthetic pathway that enables the tailoring of both the oxygen sensing molecules' oxygen sensitivity range and the oxygen sensing molecules' compatibility with the matrix material the oxygen sensing molecules can be embedded in. The matrix material can further be configured to tailor the oxygen sensing molecules' oxygen sensitivity range. The oxygen sensing molecules can be specifically designed to feature bright, red phosphorescence emission, with a visual response to changes in oxygenation level that can be seen under ambient light. These properties simplify the collection and interpretation of their oxygen-dependent emission, enabling the analysis to be performed with simple and inexpensive equipment.

In some embodiments, the probe 24 can comprise a porphyrin described in U.S. Patent Application Publication No. 2016/0159842, which is incorporated herein by reference. For example, the porphyrin may be an oxygen-sensitive phosphor whose emission intensity is dependent on oxygen partial pressure.

In one embodiment, the probe 24 comprises a phosphorescent meso-unsubstituted porphyrin having the Formula (I):

(I)

wherein M is a metal, wherein each R is independently an atom or a group of atoms, and wherein at least one R is —OR$^1$, wherein R$^1$ is an atom or a group of atoms.

In the porphyrin of Formula (I), R$^1$ may be selected from the group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, halo, cyano, and nitro. In one example of the porphyrin of Formula (I), R$^1$ is hydrogen. In another example of the porphyrin of Formula (I), R$^1$ is alkynyl, such as 2-propynyl (propargyl). In the porphyrin of Formula (I), a plurality of R can be —OR$^1$, and optionally, every R can be —OR$^1$.

In one example of the porphyrin of Formula (I), R$^1$ includes a triazolyl group. The triazolyl group may be bonded to O via an alkyl chain. In one example of the porphyrin of Formula (I), R$^1$ includes an alkylglutamate group. R$^1$ may terminate in a pair of alkylglutamate groups. In another example of the porphyrin of Formula (I), R$^1$ includes a triazolyl group, and R$^1$ terminates in a pair of ethylglutamate groups, and every R is —OR$^1$. In one example of the porphyrin of Formula (I), the metal is platinum or palladium.

The porphyrin of Formula (I) may be an oxygen-sensitive phosphor whose emission intensity is dependent on oxygen partial pressure. In one example of the porphyrin of Formula (I), the porphyrin can be excited when illuminated at a first wavelength in a range of 350-600 nanometers, followed by emission of phosphorescence at a second wavelength in a range of 600-700 nanometers. The first wavelength can be 532 nanometers, and the second wavelength can be 644 nanometers. The first wavelength can also be 546 nanometers and the second wavelength can be 674 nanometers.

In another embodiment, the probe 24 comprises a phosphorescent meso-unsubstituted porphyrin having the Formula (II):

(II)

In the porphyrin of Formula (II), R$^1$ may be selected from the group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, halo, cyano, and nitro. In one example of the porphyrin of Formula (II), $R^1$ is hydrogen. In another example of the porphyrin of Formula (II), $R^1$ is alkynyl, such as 2-propynyl (propargyl). In the porphyrin of Formula (I), a plurality of R can be —$OR^1$, and optionally, every R can be —$OR^1$.

In one example of the porphyrin of Formula (II), $R^1$ includes a triazolyl group. The triazolyl group may be bonded to O via an alkyl chain. In one example of the porphyrin of Formula (II), $R^1$ includes an alkylglutamate group. $R^1$ may terminate in a pair of alkylglutamate groups. In another example of the porphyrin of Formula (II), $R^1$ includes a triazolyl group, and $R^1$ terminates in a pair of ethylglutamate groups, and every R is —$OR^1$. In one example of the porphyrin of Formula (II), the metal is platinum or palladium.

The porphyrin of Formula (II) may be an oxygen-sensitive phosphor whose emission intensity is dependent on oxygen partial pressure. In one example of the porphyrin of Formula (II), the porphyrin can be excited when illuminated at a first wavelength in a range of 350-650 nanometers, followed by emission of phosphorescence at a second wavelength in a range of 700-800 nanometers. The first wavelength can be 594 nanometers, and the second wavelength can be 740 nanometers. The first wavelength can be 605 nanometers, and the second wavelength can be 770 nanometers. The first wavelength can also be 600-615 nanometers and the second wavelength can be 760-800 nanometers.

Figure 2:
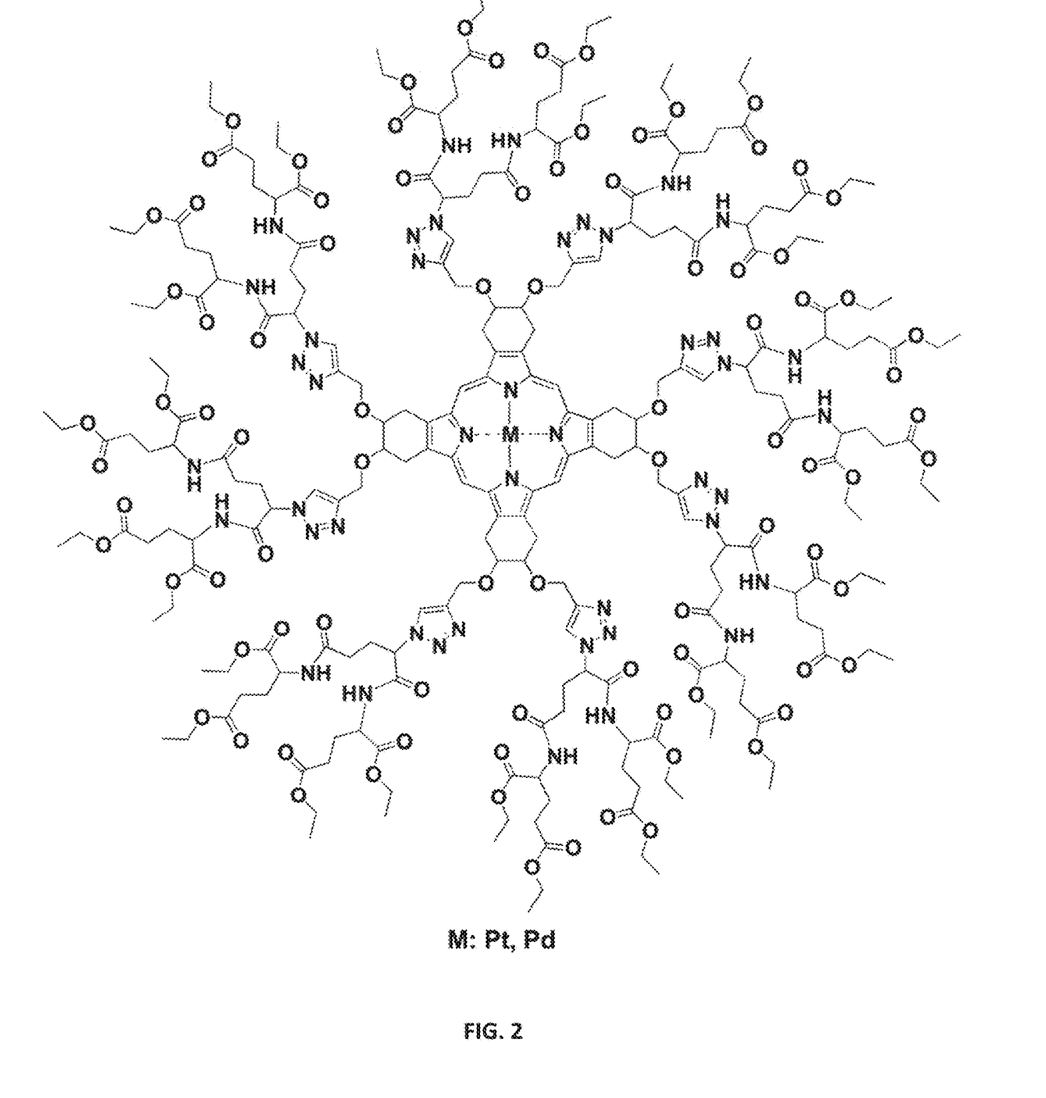
FIG. 2 is a diagram of an exemplary structure metallated porphyrin-dendrimer that may be employed as the probe of an oxygenation monitor of the present disclosure.

As a specific non-limiting example, the probe 24 comprises a brightly emissive, custom built meso-unsubstituted platinum-porphyrin that is encapsulated inside a second generation glutamic dendrimer, as illustrated in FIG. 2. In this example porphyrin of FIG. 2, the probe 24 can be excited when illuminated at 532 nanometers, followed by emission of phosphorescence at 644 nanometers whose intensity can be used as an indicator for oxygen concentration.

A circuit board 38 containing the emission sources 28 and the detectors 32 can be attached to the probe 24. In some embodiments, the circuit board 38 can be attached to the probe 24 on an opposite side of the interface mechanism 36 of the probe 24 on a surface of the probe 24 via an oxygen-impermeable membrane. In some embodiments, the circuit board can be linked to the probe 24 via optical fibers 54. The circuit board 38 can be flexible and can have a substrate, wherein the emission sources 28 and the detectors 32 can be embedded in or on the substrate.

The emission sources 28 can be positioned in or on the substrate such that each emission source 28 is positioned to emit photons directed at the probe 24. In an exemplary, non-limiting embodiment, the emission sources 28 are positioned at four radial positions around the circuit board 38 such that the emission sources 28 can direct photons to the probe 24. In some embodiments, the emission sources 28 can be a blue light-emitting diode. In other embodiments, the emission sources 28 can be an orange light-emitting diode. In other embodiments, the emission sources 28 can be optical fibers that deliver specific colors of light.

The detectors 32 can be positioned in or on the substrate such that each of the detectors 32 is positioned to detect or receive photons emitted from the probe 24. In an exemplary, non-limiting embodiment, the detectors 32 are positioned at four radial positions around the circuit board 38 such that the detectors 32 can detect or receive photons emitted from the probe 24. The detectors 32 on the circuit board 38 can comprise one or more green photodetectors and/or one or more red photodetectors. In some embodiments, the detectors 32 can be a photodiode. The one or more green photodetectors can be green photodiodes, and the one or more red photodetectors can be red photodiodes. In other embodiments, the detectors 32 can be a charge-coupled device (CCD). In other embodiments, the detectors 32 can be optical fibers that couple emitted light to photodetectors, including photodiodes and charge-coupled devices (CCDs). In other embodiments, the photodetectors can detect both green and red emission.

The circuit board 38 can also comprise a controller 44 that can be in electrical communication with the emission sources 28 and the detectors 32. The controller 44 can be a microcontroller, or system-on-a-chip, and can comprise a memory which can be a non-transitory memory that can store executable programs on the controller 44. In some embodiments, the controller 44 can store an oxygen calculation program that can calculate a level of oxygen adjacent the probe 24 from one or more electrical signals received from the detectors 32. The circuit board 38 can also include an output 48, which can be a wire bundle. The output 48 can connect to an external interface which can be used for at least one of displaying, storing, and analyzing the results of the executable program of the optical TCOM system 20. In other embodiments, the controller 44 can be configured to have a wireless output; the wireless output can perform wireless communication. Non-limiting examples of wireless communication that can be incorporated are Wi-Fi, Bluetooth®, near-field communication, cellular network, radio-frequency, etc. The circuit board 38 can comprise an on-board power source, for example a battery, that can provide power to the circuit board 38 such that the emission sources 28, the detectors 32, and the controller 44 can be powered. In other embodiments, the circuit board 38 can comprise an external power source, for example electrical connection to grid power, that can provide power to the circuit board 38 such that the emission sources 28, the detectors 32, and the controller 44 can be powered.

Now that the components of the optical TCOM system 20 have been described in detail, the function of the components of the optical TCOM system 20 can be understood. In some embodiments, the probe 24 can be placed in contact with a tissue of the patient via the interface mechanism 36. In some embodiments, the probe 24 can be an oxygen-sensing polymer that can be positioned to be in contact with or coincident with the interface surface 36 of the optical TCOM system 20 such that the probe 24 can be in direct contact with the tissue of the patient. Direct contact between the probe 24 and the tissue of the patient can allow for the probe 24 to provide tissue $pO_2$ via the photoluminescent oxygen sensing formulation of the probe 24. The photoluminescent oxygen sensing formulation of the probe 24 can have an emission that can be indicative of the tissue $pO_2$.

The photoluminescent oxygen sensing formulation of the probe 24 can emit red phosphorescence when excited by blue light from one or more of the emission sources 28, with a phosphorescence intensity detected by one or more of the detectors 32. The phosphorescence intensity can be inversely proportional to $pO_2$ of the tissue of the patient. The reference sensor, which can be in the form of a green-emitting dye, can also be loaded into the probe 24 and can serve as a reference standard for precise $pO_2$ measurements. The phosphorescence lifetime can be measured and analyzed to provide precise $pO_2$ measurements. The circuit board 38 can be flexible and can be attached to a surface of the probe 24 via an oxygen-impermeable membrane. The circuit board 38 can contain emission sources 28 and detectors 32. The emission sources 28 can be one or more blue light emitting diodes (LEDs), and the detectors 32 include one or more green photodetectors in the form of green sensitive photodiode detectors and one or more red photodetectors in the form of red sensitive photodiode detectors. In some embodiments, the detectors can be a photodiode, photomultiplier tube, avalanche photodiode, charge-coupled device (CCD), complementary metal-oxide semiconductor (CMOS) device, or combination of similar photodetectors.

The oxygen-dependent change in red phosphorescence intensity, can be captured by the red photodetectors in the form of red sensitive photodiode detectors and referenced against the green emission captured by the green photodetectors in the form of green sensitive photodiode detectors using analog circuitry of the controller 44 to provide pre-calibrated, robust transcutaneous oxygen tension measurements of the tissue of the patient.

The analog or digital circuitry of the controller 44 can provide pre-calibrated, robust transcutaneous oxygen tension measurements of the tissue of the patient. In some embodiments, the oxygen tension measurements can be analyzed and reported by utilizing molecules (e.g. fluorophore probes) whose emission properties are insensitive to oxygen along with molecules (e.g., phosphor probes) whose emission properties are influenced by molecular oxygen concentration. The molecules whose emission properties are insensitive to oxygen can be the reference sensor, and the molecules whose emission properties are influenced by molecular oxygen concentration can be the phosphor probes. Emission from the fluorophore probes and phosphor probes can be used to measure oxygen tension in biological systems reversibly with high fidelity. The fluorophore probes and phosphor probes can be calibrated so that a spectral ratio between fluorophore and phosphor emission correlates with oxygen concentration of the tissue of the patient. The calibration can be used to read out a map of oxygen concentration in the tissue of the patient. The calibration can also be used to read out an average oxygen concentration of the area covered by the optical TCOM system 20. The fluorophore probes and phosphor probes can be calibrated so that the lifetime of the fluorophore and phosphor emission can be analyzed to provide the oxygen concentration of the tissue of the patient. It is also possible to utilize molecules such as dyes whose light absorption properties (such as, absorption wavelength or absorption cross-section) can be modulated by the presence of analytes such as oxygen for light absorption-based colorimetric oxygen measurements.

In one embodiment, the analog or digital circuitry of the controller 44 can provide pre-calibrated, robust transcutaneous oxygen tension measurements and analysis of the tissue of the patient using the Stern-Volmer relationship. The Stern-Volmer relationship can be used to characterize the oxygenation of the tissue of the patient based on the photoluminescent oxygen sensing formulation of the probe 24 that can emit red phosphorescence when excited by blue light from the at least one emission source 28, with a phosphorescence intensity detected by the at least one detector 32 can be inversely proportional to $pO_2$ of the tissue of the patient. A dynamic (collisional) quenching by oxygen is a photophysical (rather than a photochemical) process. It is fully reversible, does not alter the optical probe, and thus has no effect on its absorption spectrum. Rather, it leads to a drop in luminescence intensity and luminescence lifetime. The relationship between intensity (or decay time) and the concentration of oxygen ($[O_2]$) is reflected by the Stern-Volmer equation which, in its most simple form, reads as:

$$\frac{F_0}{F} = \frac{\tau_0}{\tau} = 1 + K_{SV}[O_2]$$

Where $F_0$ and $F$, respectively, are the luminescence intensities of a probe in the absence and presence of oxygen, $\tau_0$ and $\tau$, respectively, are the luminescence lifetimes of a probe in the absence and presence of oxygen, $K_{SV}$ is the Stern-Volmer constant which is a function of the lifetime of the probe and its environment (polymeric matrix, solvent, etc.), and $[O_2]$ is the concentration of oxygen in the sample. The term $[O_2]$ (a concentration) may be replaced by $pO_2$, the partial pressure of oxygen.

In some embodiments of the optical TCOM system 20, there can be a linear relationship between $F_0/F$ (or $\tau_0/\tau$) and oxygen concentration. Stern-Volmer plots (SVPs) can be established by measurement of either luminescence intensity or decay time. However, luminescence intensity data can be adversely affected by poor stability of the light source, variations in the efficiency of the transmission optics, drifts in detector sensitivity, leaching and photodecomposition of probes, inhomogeneous probe distribution, background luminescence and stray light. In order to correct for these effects, a reference sensor (e.g. an inert reference fluorophore emitting at a different wavelength) can be used.

In some embodiments, the controller 44 can analyze the ratio of red emissions compared to green emissions internally to determine the oxygen concentration of the tissue of the patient. In other embodiments, the optical TCOM system 20 can communicate emission results acquired from the at least one detector 32 externally to be analyzed by an external device.

In some embodiments, the optical TCOM system 20 can also comprise a display 56. The display can be configured to indicate the oxygenation of the tissue of the patient as determined by the optical TCOM system 20. In some embodiments, the display can be attached to the optical TCOM system 20, while in other embodiments, the display can be positioned externally from the optical TCOM system 20.

In some embodiments, the optical TCOM system 20 can be an implantable device that can interface with internal tissues of the patient. In other embodiments, portions of the optical TCOM system can be implantable while other portions remain outside of the patient. In other embodiments, the optical TCOM system can be positioned on a medical instrument in order to determine oxygen levels during a surgical procedure. A non-limiting example of a medical instrument can be a catheter 62, where the tip of the catheter can comprise the optical TCOM system to determine the oxygenation of the tissue in contact with the tip of the catheter.

In some embodiments, the optical TCOM system 20 can be disposable such that a patient can wear the optical TCOM on a tissue of the patient for a period of time. A non-limiting example of a period of time being 1-7 days. After the period of time has elapsed, the patient can dispose of the optical TCOM system 20.

In some embodiments, the optical TCOM system 20 can continuously monitor and report oxygenation of the tissue of the patient. In other embodiments, the optical TCOM system 20 can include an on-off switch that can determine when an oxygenation reading can be taken. In other embodiments, the optical TCOM system 20 can have a scheduled sampling rate where the optical TCOM system 20 can supply oxygenation readings at predetermined time intervals.

Accordingly, an advantage of this disclosure can be an all-in-one adhesive optical TCOM system 20 that can require minimal to no calibration, minimal user training, no heating of the measurement site, no exogenous agents, and can acquire tissue oxygenation readings immediately upon application.

Accordingly, another advantage of this disclosure can be the optical TCOM system 20 can be able to operate at normal skin temperature and can be worn without restrictions in patient mobility. As a result of its versatility, the optical TCOM system 20 may replace current TCOM tools in all clinical settings, from the ICU to outpatient care. Some target populations for the optical TCOM system 20 can comprise in-patients undergoing procedures that seek to maintain or restore tissue perfusion and physiological function, such as transplants, reconstruction, and vascular surgeries, as well as interventions for patients at high risk of developing chronic wounds from dysfunctional circulation or other post-surgical complications. There is a particular need for this technology for patients who would suffer from chronic wounds, with utilities ranging from the detection of poor perfusion to prevent pressure and diabetic ulcers, to aiding a surgeon in making key limb salvage decision in the operating room. Existing TCOM devices are not robust, are difficult to use, require skilled technicians, and take more than a half hour for a single measurement: this solution overcomes these limitations to make TCOM simple, easy, and accurate for improved patient care.

As the above patient groups are in need of long-term monitoring through multiple settings, we envision another advantage of this disclosure can be the optical TCOM system 20 can be the reduced need for multiple sensor applications in the monitoring process. A single optical TCOM system 20, which can be a sensor patch can be applied and remain attached and fully functional even when a patient changes position or is moved through settings. This is not possible with current TCOM devices, as it is necessary to remove the sensor before moving the patient and then re-apply and possibly repeat the calibration before acquiring new measurements. Additional benefits of this disclosure can include the minimal need for training or retraining of hospital staff, the reduction in time and effort put into acquiring tissue oxygenation data by hospital staff, and the limited need for the involvement of highly skilled physicians during post-operative monitoring. By improving on TCOM technology and delivering a replacement optical TCOM system 20 that is easier to use while still retaining the utility and clinician familiarity of existing TCOM devices, these benefits will amount to a significantly reduced cost to the healthcare system.

Accordingly, another advantage of this disclosure can be success in measuring tissue oxygenation, using silicone plastic sensors that display the same sensitivity and dynamic range to physiological oxygen tension. These PDMS-based materials can be readily functionalized with adhesives to provide a simple-to-use oxygen-sensing patch. The brightness and visible red emission of the sensing molecules can allow for simplified oxygen readout accomplished either through implanted optical fibers, or through electronic detection via an LED/photodiode interface directly coupled to the sensor.

Accordingly, another advantage of this disclosure can be the versatility of the optical TCOM system 20 that can enable its applications to extend beyond the initial in-patient focus population. One area of interest can be the monitoring of oxygenation in neonatal care units, which is what TCOM technology was originally developed to target. A benefit for this particular application can be the elimination of the tissue heating step now required when using current TCOM devices which can cause burns on the sensitive skin of neonates. The optical TCOM system 20 can also allow for wireless optical TCOM $pO_2$-monitoring for patients with mobility problems, such as those with prosthetics, those restricted to wheelchairs, or the bedridden. The wireless optical TCOM system 20 can enable the monitoring of tissue regions that are currently only accessible by moving the patient, making the optical TCOM system 20 a prognostic indicator of early signs of abnormal oxygenation that could lead to the development of chronic conditions caused by prolonged immobility.

Another advantage of this disclosure can be time savings since a doctor or nurse would no longer have to order a TCOM placed, wait for a technician to setup and calibrate the device, and then wait an additional half hour for a result; instead the optical TCOM system 20 can be placed on the tissue and begin reporting immediately, to either a dedicated device or generic or multipurpose device such as a smartphone. The optical TCOM system 20, which can be adhered to the skin and thus can be insensitive to motion and patient movement, can make oxygenation measurements straightforward and robust. This approach minimizes interference from common patient comorbidities, problems arising from device placement, or environmental conditions confounding oxygenation readout. The improved TCOM device can provide clinical caregivers with more accurate information, leading to improved decision-making, better patient outcomes, and fewer readmissions.

Another advantage of this disclosure can be a better mechanism for assessing tissue oxygenation that leads to better, more rapid care, and it can be the difference between saving and losing a limb. Diabetic patients, in particular, suffer from chronic poor perfusion in limbs that too often require amputation. Patients and clinicians both want to salvage as much tissue as possible in hopes of retaining function and mobility, but under-amputating and readmitting for a second amputation carries enormous morbidity. Finding the right balance between salvage and amputation depends entirely on perfusion and oxygenation of the limb, which is notoriously difficult to assess in ischemic conditions and chronic wounds. Unlike the current metrics in use—pulse volume recording, Doppler flow and pressure measurements, angiography, and capillary refill—the new optical TCOM system 20 does not rely on the presence of blood flow, and could be much more effective at determining tissue status in these difficult-to-treat patients.

Another advantage of this disclosure is the optical TCOM system 20 can have numerous applications addressing clinical, ambulatory, field, and even industrial needs. There are a number of scenarios in which a caregiver may wish to rapidly assess the perfusion, viability, and oxygenation of a region, such as in neonatal monitoring (particularly for SIDS), dive medicine, Raynaud's disease, and scleroderma, to name only a few. By building a better optical TCOM system 20, our new technology will allow simple, easy, and accurate oxygenation measurements beyond the artificial restrictions of current TCOM devices to wherever oxygenation plays a pathogenic or diagnostic role.

The invention is further illustrated in the following Example which is presented for purposes of illustration and not of limitation.

Example

A validation study of a polymer-based, oxygen-sensing paint-on formulation against the current standard-of-care ViOptix device was performed. Validation was performed on a clinical study where transplanted tissue flaps were monitored for a 48-hour period following mastectomy and breast reconstruction surgery.

The oxygen sensitive phosphor used in creating the sensing formulation was the palladium (Pd) containing version of the porphyrin-dendrimer shown in FIG. 2. The reference dye used in the sensing bandage was the FDA-approved, green-emitting dye fluorescein. A paint-on formulation mixture was formulated by mixing the oxygen sensitive phosphor, the reference dye, and a liquid bandage (including solvent and nitrocellulose). A breathable transparent film dressing was used as the barrier layer covering the sensing formulation to reduce the oxygen exchange between the sensing bandage and room air. Electronic flash units were used to provide a brief pulse of blue excitation light ($\lambda_{ex}$=385 nm; 70 nm bandwidth) for both the oxygen-sensing phosphor and the reference dye. A CMOS camera was used to collect the emitted light from the sensing bandage. The phosphorescence of the oxygen sensitive phosphor was captured as the "red-channel" image. The reference dye was imaged as the "green-channel". Images were captured on the two channels by switching between a red ($\lambda_{em}$=660 nm; 40 nm bandwidth) and a green ($\lambda_{em}$=525 nm; 30 nm bandwidth) filter in front of the camera lens.

Figure 3:
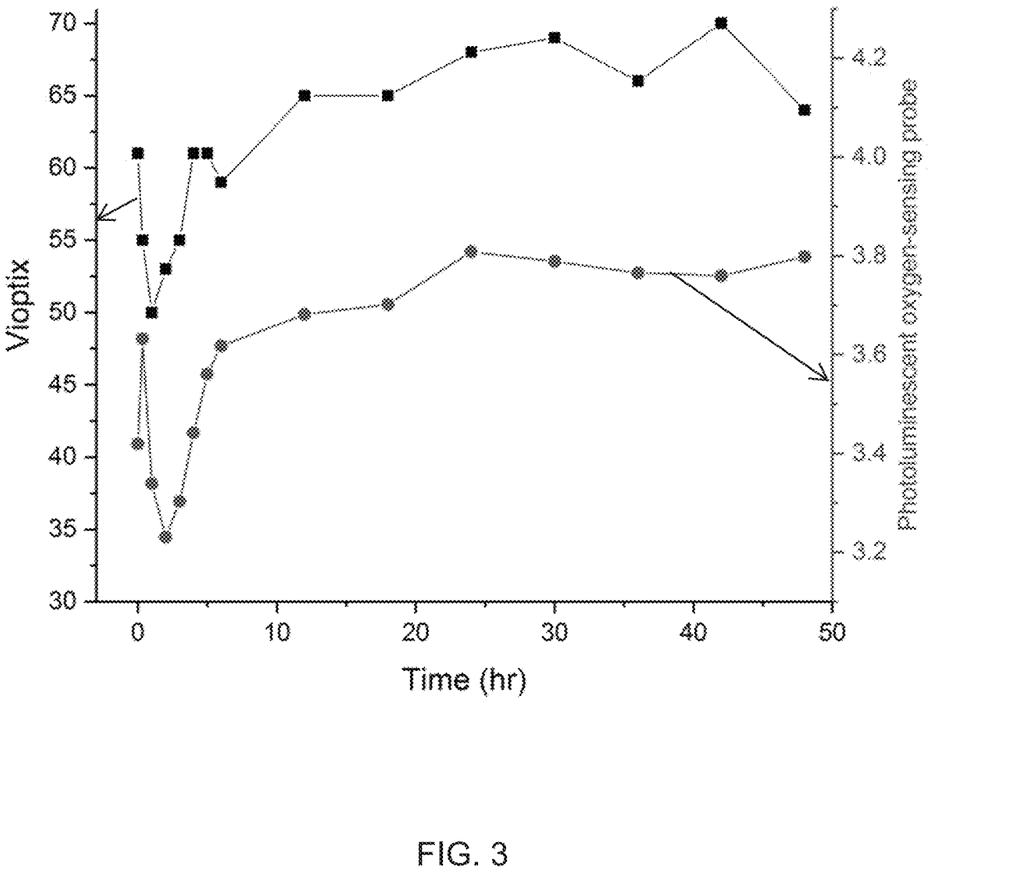
FIG. 3 shows the validation of a polymer-based, oxygen-sensing system against the current standard-of-care ViOptix device.

In FIG. 3, the left vertical axis is in units of $StO_2$ (%), and the right vertical axis is the inverse of the ratio of red phosphorescence over total luminescence (red phosphorescence plus reference green fluorescence). The plots in FIG. 3 show that the photoluminescent oxygen-sensing formulation of this Example can accurately reflect the drop and recovery in the flap oxygenation measured by the current standard-of-care ViOptix device.

Thus, the invention provides systems and methods of oxygenation monitoring, specifically optical transcutaneous oxygenation monitoring.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the embodiments contained herein.

What is claimed is:

1. An oxygenation monitor for use with a photoluminescent oxygen-sensitive probe, the oxygenation monitor comprising:
   a photoluminescent oxygen-sensitive probe;
   a photon source configured to direct photons at the probe;
   a photodetector configured to detect light emitted from the probe when the photon source directs photons at the probe;
   a reference sensor providing a reference for calibrating the photoluminescent oxygen-sensitive probe;
   a controller in electrical communication with the photon source and the photodetector, the controller being configured to execute a program stored in the controller to calculate a level of oxygen adjacent the probe from an electrical signal received from the photodetector; and
   a support structure,
   wherein the photon source, the photodetector, and the controller are disposed in or on the support structure, and
   wherein the controller is configured to execute the program stored in the controller to provide pre-calibrated, transcutaneous oxygen tension measurements of a tissue of a patient using a Stern-Volmer relationship and applying the reference for calibrating the photoluminescent oxygen-sensitive probe for the oxygen tension measurements,
   wherein the oxygenation monitor requires no heating of a measurement site to acquire tissue oxygenation readings.

2. The oxygenation monitor of claim 1 wherein:
the photoluminescent oxygen-sensitive probe is a formulation having an emission that provides tissue $pO_2$.

3. The oxygenation monitor of claim 1 wherein:
the photoluminescent oxygen-sensitive probe comprises a polymeric material impregnated with a porphyrin.

4. The oxygenation monitor of claim 1 wherein:
the photoluminescent oxygen-sensitive probe emits a red phosphorescence when excited by blue light from the photon source.

5. The oxygenation monitor of claim 1 wherein:
the support structure comprises a flexible circuit board attached to a surface of the photoluminescent oxygen-sensitive probe via an oxygen-impermeable membrane.

6. The oxygenation monitor of claim 1 wherein:
a phosphorescence intensity detected by the photodetector is inversely proportional to $pO_2$ of a tissue of a patient.

7. The oxygenation monitor of claim 1 wherein:
an oxygen-dependent change in phosphorescence lifetime is captured by the one or more photodetectors, the oxygen-dependent change in phosphorescence lifetime is analyzed to provide transcutaneous oxygen measurements of a tissue of a patient.

8. The oxygenation monitor of claim 1 wherein:
the level of oxygen adjacent to the probe is reported by utilizing one or more fluorophore probes and one or more emission properties of the one or more fluorophore probes are insensitive to oxygen.

9. The oxygenation monitor of claim 1 wherein:
the level of oxygen adjacent to the probe is reported by utilizing one or more phosphor probes, and one or more emission properties of the one or more phosphor probes are influenced by molecular oxygen concentration.

10. The oxygenation monitor of claim 1 further comprising:
a display in electrical communication with the controller, wherein the controller is configured to execute the program stored in the controller to display the level of oxygen on the display.

11. The oxygenation monitor of claim 1 wherein:
the controller is configured to execute the program stored in the controller to store values of the level of oxygen at a plurality of times over a time period.

12. The oxygenation monitor of claim 1 further comprising:
a display in electrical communication with the controller, wherein the controller is configured to execute the program stored in the controller to display values of the level of oxygen at a plurality of times over a time period.

13. The oxygenation monitor of claim 1 wherein:
the oxygenation monitor is implantable in a body part of a patient.

14. The oxygenation monitor of claim 1 further comprising:
a light guide for directing photons from the photon source at the probe.

15. The oxygenation monitor of claim 14 wherein:
the light guide is an optical fiber.

16. The oxygenation monitor of claim 1 further comprising:

a light guide for directing light emitted from the probe at the photodetector.

17. The oxygenation monitor of claim 16 wherein:
the light guide is an optical fiber.

18. The oxygenation monitor of claim 1 wherein:
the photoluminescent oxygen-sensing probe can comprise both a red-emitting oxygen sensitive probe and a green-emitting reference dye, both the red-emitting oxygen sensitive probe and the green-emitting reference dye are simultaneously excited by blue light from the photon source.

19. The oxygenation monitor of claim 1 wherein:
the support structure is made by an oxygen-impermeable material to serve as an impermeable membrane.

20. A kit for monitoring oxygenation, the kit comprising:
the oxygenation monitor of claim 1;
optionally one or more additional photoluminescent oxygen-sensitive probes,
wherein each photoluminescent oxygen-sensitive probe is structured to be removably attached to the support structure.

21. The kit of claim 20 wherein:
each photoluminescent oxygen-sensitive probe is provided in a package that does not transmit photons of a wavelength that causes emission of light by the probe.

22. The kit of claim 21 wherein:
the package includes an indicator of the useful lifetime of the photoluminescent oxygen-sensitive probe.

23. A device comprising:
a medical instrument; and
the oxygenation monitor of claim 1, the oxygenation monitor being attached to the medical instrument.

24. The oxygenation monitor of claim 1 wherein:
the Stern-Volmer relationship includes at least one variable which is a function of an environment of the photoluminescent oxygen-sensitive probe.

25. The oxygenation monitor of claim 24 wherein:
the reference sensor can be used to correct for effects of the environment.

26. The oxygenation monitor of claim 24 wherein:
the environment is adjacent to a body part of a patient.

27. The oxygenation monitor of claim 24 wherein:
the environment is adjacent to skin of a patient.

28. The oxygenation monitor of claim 24 wherein:
the environment has a temperature.

29. The oxygenation monitor of claim 28 wherein:
the pre-calibrated, transcutaneous oxygen tension measurements account for the temperature.

30. The oxygenation monitor of claim 1 wherein:
the pre-calibrated, transcutaneous oxygen tension measurements account for dynamic collisional quenching by oxygen.

* * * * *